United States Patent [19]

Boland et al.

[11] Patent Number: 4,834,736

[45] Date of Patent: * May 30, 1989

[54] DISPOSABLE ABSORBENT GARMENT HAVING ELASTIC OUTER COVER AND ABSORBENT INSERT STRUCTURE INTEGRATED THEREIN USING STRESS-RELEASE MEANS

[75] Inventors: Leona G. Boland, Neenah; Georgia L. Zehner, Larsen; Robert A. Stevens, Appleton, all of Wis.

[73] Assignee: Kimberly-Clark Corporation, Neenah, Wis.

[ * ] Notice: The portion of the term of this patent subsequent to Oct. 20, 2004 has been disclaimed.

[21] Appl. No.: 34,817

[22] Filed: Apr. 3, 1987

[51] Int. Cl.⁴ .............................................. A61F 13/16
[52] U.S. Cl. ................................... 604/385.2; 604/389
[58] Field of Search ............... 604/385 A, 385 R, 370, 604/372, 378, 389, 390, 395, 399

[56] References Cited

U.S. PATENT DOCUMENTS

| | | | |
|---|---|---|---|
| 2,141,105 | 12/1938 | Eller et al. | 128/284 |
| 3,196,874 | 7/1965 | Hrubecky | 128/287 |
| 3,370,590 | 2/1968 | Hokanson et al. | 128/290 |
| 3,644,157 | 2/1972 | Draper | 156/160 |
| 3,658,064 | 4/1972 | Pociluyko | 128/287 |
| 3,995,640 | 12/1976 | Schaar | 604/385.2 |
| 4,050,462 | 9/1977 | Woon et al. | 128/287 |
| 4,166,464 | 9/1979 | Korpman | 128/287 |
| 4,182,334 | 1/1980 | Johnson | 604/385 A |
| 4,324,245 | 4/1982 | Mesek et al. | 128/287 |
| 4,355,425 | 10/1982 | Jones et al. | 2/402 |
| 4,381,781 | 5/1983 | Sciaraffa et al. | 604/372 |
| 4,397,646 | 8/1983 | Daniels et al. | 604/381 |
| 4,425,128 | 1/1984 | Motomura | 604/381 |
| 4,496,360 | 1/1985 | Joffe et al. | 604/397 |
| 4,527,990 | 7/1985 | Sigl | 604/385 |
| 4,597,760 | 7/1986 | Buell | 604/397 |
| 4,597,761 | 7/1986 | Buell | 604/397 |

Primary Examiner—C. Fred Rosenbaum
Assistant Examiner—Denise Whelton
Attorney, Agent, or Firm—John L. Chiatalas

[57] ABSTRACT

An anatomically form-fitting, generally self-adjusting disposable absorbent garment comprising a breathable elastomeric nonwoven laminar outer cover having an absorbent insert structure attached and integrated thereinto while allowing substantially unrestricted functional stretchability of the outer cover. The insert is attached to the outer cover by selectively breakable sonic bonds along either of the waist and leg openings of the outer cover to accommodate various body shapes and sizes. Upon exertion of certain stresses against the garment by wearers having larger waist and/or leg sizes, the bonds break away and restore the inherent stretch properties of the corresponding region of the outer cover. The breakable bonds also maintain a neat, aesthetic appearance of the product and minimize interference of loose, unattached material during processing, storage and use of the article.

10 Claims, 5 Drawing Sheets

DISPOSABLE ABSORBENT GARMENT HAVING ELASTIC OUTER COVER AND ABSORBENT INSERT STRUCTURE INTEGRATED THEREIN USING STRESS-RELEASE MEANS

TECHNICAL FIELD

The present invention relates, generally, to the field of disposable garments utilized for the absorption and containment of urine and other bodily exudates. More particularly, the present invention relates to form-fitting, generally self-adjusting disposable absorbent garments, such as disposable diapers, training pants, incontinent garments and the like.

BACKGROUND OF THE INVENTION

Disposable garments are generally well known in the art and have become an important and an essentially indispensable sanitary protection item, most particularly in the field of infant and child care where disposable diapers provide for the absorption and containment of urine and other bodily exudates. Present commercially available disposable diapers are generally unitary, preshaped and prefolded, and comprised of a porous facing layer and a fluid impervious backing sheet with an absorbent material disposed therebetween. These presently available disposable diapers have met a particular need and have become ever increasingly popular. However, even though the present available disposable diapers have achieved a certain degree of efficiency and effectiveness, several draw-backs remain tat have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children looking rumpled, bulky or messy. In addition, these mothers have expressed the desire to either have a disposable diaper that fits more sizes of babies or to have disposable diapers provided in more sizes. Another draw-back identified by these mothers has been the problem associated with skin irritation caused by urine, feces or moisture trapped next to the skin. They have again been very vocal in their desire to obtain disposable diapers that avoid or solve this problem.

The typical disposable diaper has a three-layer composite structure comprising a liquid permeable bodyside inner liner, a liquid impermeable outer cover and an absorbent batt sandwiched between the liner and the cover. Materials now in general use for the three principal elements of a disposable diaper include various types of nonwoven fabrics for the bodyside liner, a thin thermoplastic film for the outer cover and cellulosic fluff for the absorbent batt.

Disposable diapers of the type presently on the market are flat open-sided garments that are intended to be fit around an infant by a parent while the infant is lying down. The rear panel of the diaper is placed underneath the infant, and the front panel drawn between the infant's legs, after which the sides are overlapped and held together by pressure-sensitive adhesive tape. Examples of present disposable diapers are taught in U.S. Pat. Nos. 4,324,245 to Mesek, et al., 3,196,874 to Hrubecky, and 4,050,462 to Woon, et al.

Prior art diaper constructions disclosed in the references listed below have sought to provide waste containment with a reusable diaper holder receiving an absorbent structure:

1. U.S. Pat. Nos. 3,658,064 to Pociluyko and 3,370,590 to Hokanson, et al.;
2. U.S. Pat. No. 4,425,128 to Motomura;
3. U.S. Pat. No. 2,141,105;
4. U.S. Pat. No. 4,397,646 to Daniels, et al.;
5. U.S. Patent Nos. 4,597,761, 4,496,360 and 4,597,760.

Other diapers, e.g., U.S. Pat. No. 4,166,464 to Korpman, have utilized elastic fluid impermeable backing films laminated to an absorbent layer in an attempt to provide enhanced conformability to the body surface.

U.S. Pat. Nos. 4,355,425 to Jones, et al. and 3,644,157 to Draper disclose disposable stretchable nonwoven panties unsuitable for absorbing and containing body wastes.

Even where prior art designs have attempted to use impermeable elastic film barriers, there has been inadequate recognition of the functional problems associated with an elastic outer cover. Further, costly woven diaper holders or overpants, designed to be waterproof and reusable, do not offer a truly disposable capability.

U.S. Pat. No. 4,381,781 to Sciaraffa, et al., assigned to the instant assignee, discloses an elasticized waist diaper wherein an elastic is positioned in an opening in the waist section, forming a part thereof. U.S. Pat. No. 4,527,990 to Sigl, assigned to the instant assignee, discloses an elasticized diaper wherein an elastic strip is bonded to a heat shrinkable material in the waist area.

Although the above-mentioned prior art disposable absorbent garments may be provided with elasticized leg and/or waist openings, there remains a need for an anatomically form-fitting, generally self-adjusting garment that will comfortably accommodate different body sizes and shapes.

SUMMARY OF THE INVENTION AND ADVANTAGES

According to the instant invention, there is provided an anatomically form-fitting, generally self-adjusting disposable absorbent garment comprising a breathable elastomeric nonwoven outer cover, including a pair of leg openings, front and rear waist sections together defining a waist opening, a crotch section situated between the leg openings and front and rear panels separated by the crotch section. An absorbent insert structure is substantially superposable on the front and rear panels and the crotch section, including a liquid impermeable barrier and a liquid permeable bodyside liner with an absorbent core disposed therebetween, delimiting opposed longitudinal ends and delimiting opposed lateral edges of said insert. Attachment means are provided for attaching and integrating the opposed longitudinal ends of the absorbent insert into the outer cover at selected waist attachment zones, allowing substantially unrestricted functional stretchability thereof, including stress release means for selectively detaching the insert from the outer cover to control the degree of elongation and contraction of the outer cover.

In a preferred embodiment, the insert is attached to the outer cover at selected waist attachment zones, defining one or more free-span zones underlying the absorbent insert wherein the functional stretchability of the outer cover in the free-span zone is substantially unrestricted.

In another preferred embodiment, the waist attachment zones preferably include a plurality of sonic bonds that are breakable, allowing further expansion of the waist opening to accommodate larger waist sizes.

In another preferred embodiment, the outer cover may be resiliently stretchable in an essentially cross-body direction from about 20% to about 200% and have a nonrestrictive free-span zone effectively extending at least the entire longitudinal length of the rear panel underlying the insert. The outer cover preferably comprises an elastic nonwoven web is joined to one or more gatherable nonwoven webs.

In another preferred embodiment, the absorbent structure may be integrated to the outer cover while the outer cover is in a stretched condition.

In another preferred embodiment, breakable sonic bonds are used to conceal the insert underneath the outer cover.

In a further preferred embodiment, breathable laminar nonwoven leg gathers are applied to the leg openings by breakable bonds to accommodate various leg sizes.

An advantage of the instant invention is a disposable absorbent garment having a form-fitting, generally self-adjusting fit due to an elastomeric outer cover having an integrated absorbent structure which does not inhibit the functional stretch properties of the outer cover, selectively allowing comfortable accommodation of a range of body sizes and shapes.

Another advantage of the instant invention is that the absorbent structure is held in registration with the body for absorbing and containing wastes without sagging or shifting out of place, reducing leakage from the diaper and resulting in a neat, trim fit.

A further advantage of the instant invention is the enhanced cloth-like comfort and feel of the garment while presenting a smooth pleasing appearance when worn.

DETAILED DESCRIPTION OF THE PREFERRED EMBODIMENTS

This invention is an improvement upon copending U.S. Patent Application Ser. No. 902,828 filed Sept. 3, 1986, the entire disclosure of which is hereby incorporated by reference and relied upon, teaching a garment comprising a stretchable outer cover and an absorbent insert structure attached and integrated thereinto, with refastenable closures for securing the garment about a wearer.

Figure 1:
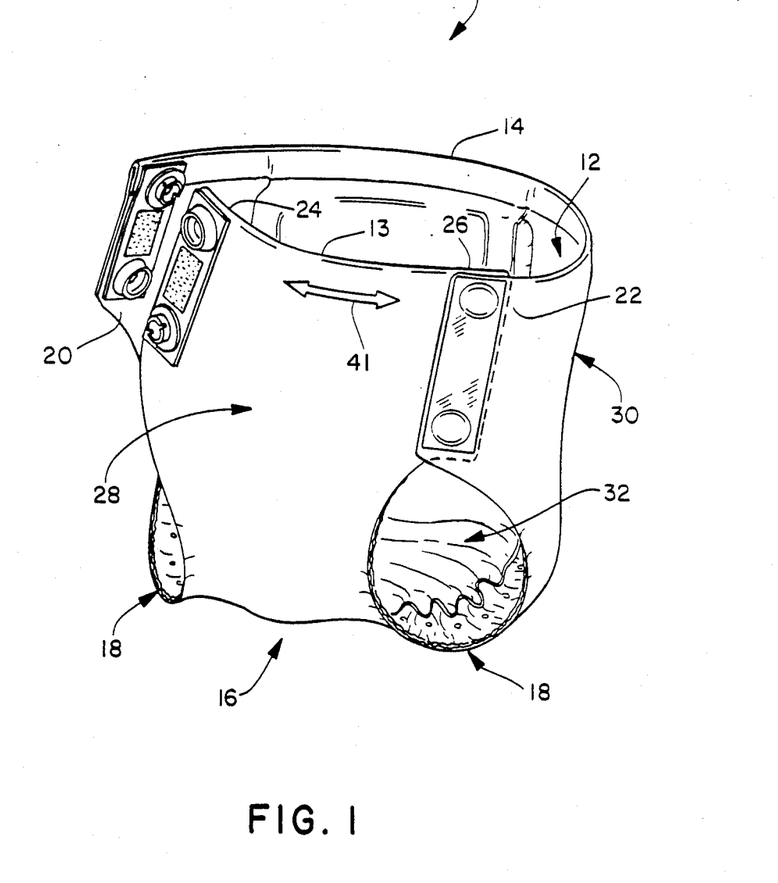
FIG. 1 is a perspective view of the invention.

Referring to FIG. 1, according to the instant invention, there is provided an anatomically form-fitting, generally self-adjusting disposable absorbent garment, generally shown at 10, such as a disposable diaper, training pant or incontinent garment, comprising an elastomeric outer cover, generally indicated at 12, including opposed front 13 and rear 14 waist sections together defining a waist opening. A crotch section, generally indicated at 16, is situated between a pair of leg openings 18 at outermost portions of said crotch section 16. Ear portions 20, 22, 24, 26 are delimited generally between the opposed waist sections 13, 14 and each of the marginal leg openings 18, respectively, with longitudinally opposed pairs of said ears 20, 24 and 22, 26 being engageable with one another about the body of a wearer. Also, the outer cover 12 preferably has a generally asymmetrical hourglass profile with the leg openings 18 cut out from the crotch section 16 thereof, defining a front panel 28 having a laterally opposed front pair of the ear portions 24, 26 in conjunction therewith and a rear panel 30 having another laterally opposed rear pair of the ear portions 20, 22 in conjunction therewith. The front 28 and rear 30 panels are separated from one another by the crotch section 16 which is narrowed due to the converging leg cut-out openings 18.

Figures 2, 2A:
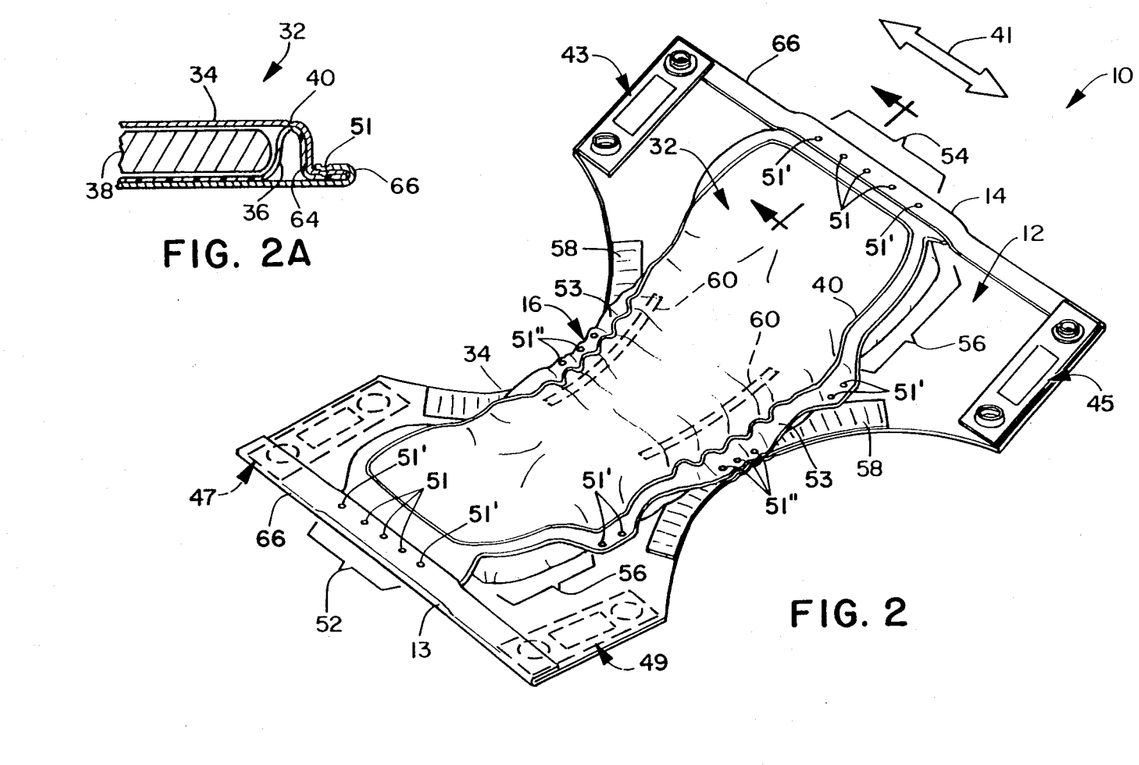
FIG. 2 is an internal perspective view of the invention.
FIG. 2A is a cross-section taken along the lines 2A—2A of FIG. 2.
Figure 3:
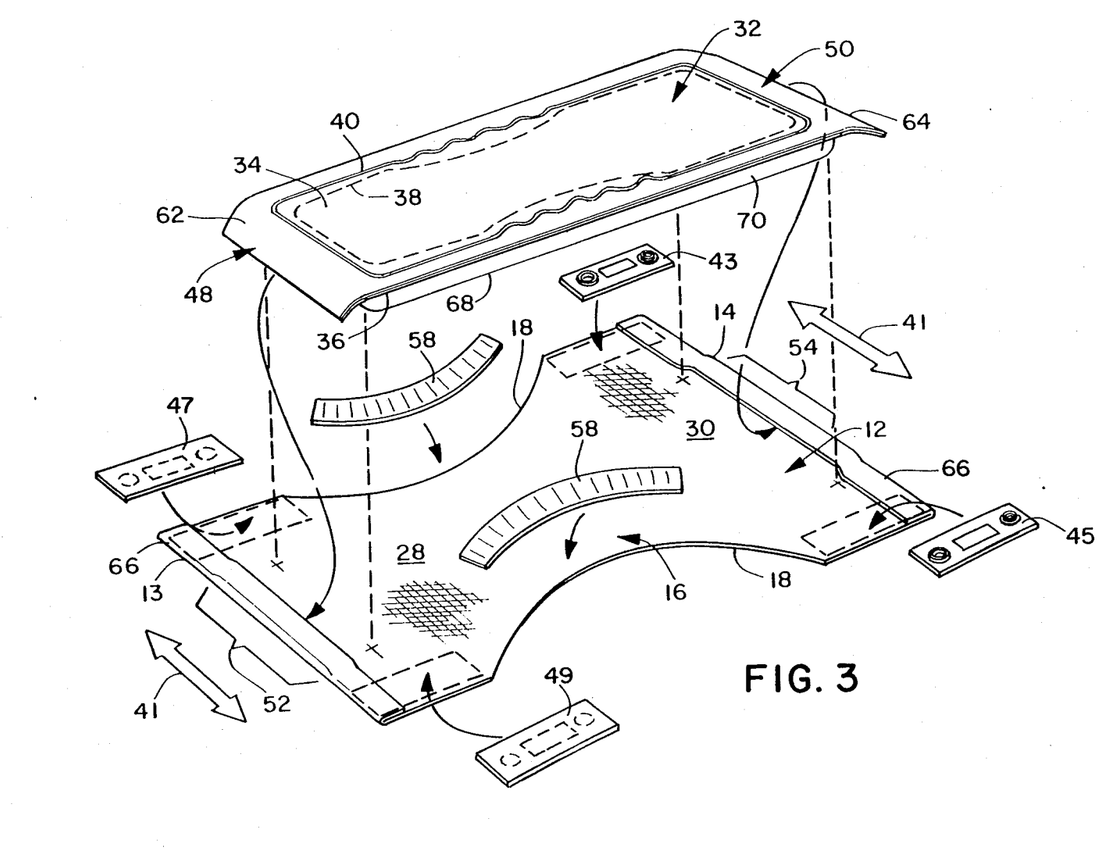
FIG. 3 is an exploded perspective view of the invention.
Figure 4:
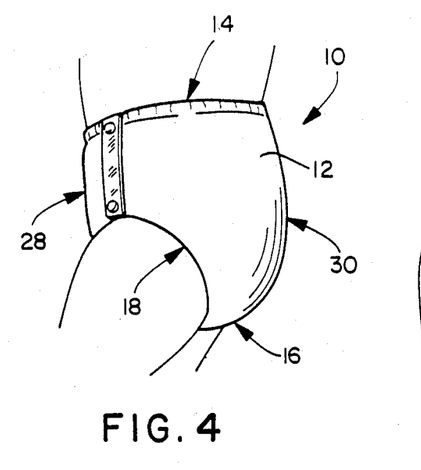
FIG. 4 is a side view of the disposable absorbent undergarment of the present invention shown secured around a baby.
Figure 5:
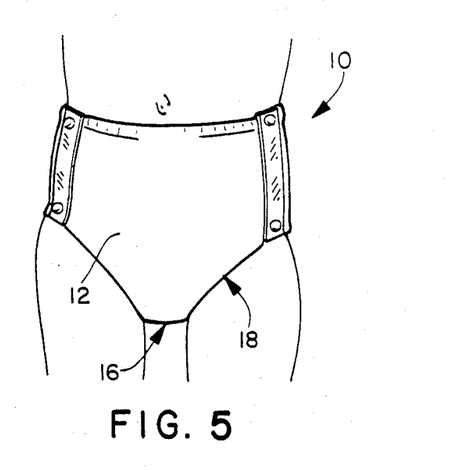
FIG. 5 is a front view of the disposable absorbent undergarment of the present invention shown secured around a baby.
Figure 6:
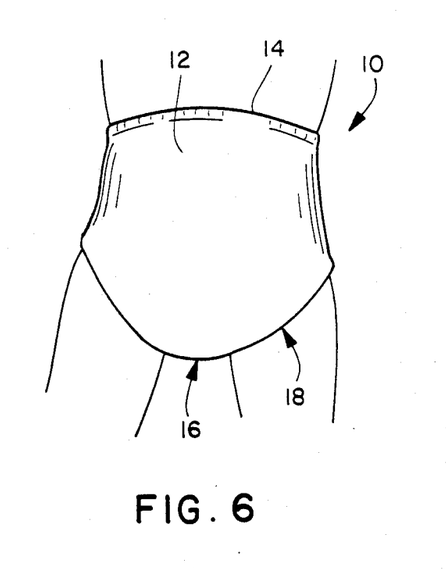
FIG. 6 is a back view of the disposable absorbent undergarment of the present invention shown secured around a baby.

With reference to FIG. 3, there is depicted an absorbent structure, generally indicated at 32, substantially superposable on the front 28 and rear 30 panels and the crotch section 16 of the outer cover 12 for absorbing and containing bodily exudates. The absorbent structure 32 includes: a liquid-permeable bodyside liner 34, for example, a commercially available pattern-bonded, spunbonded polypropylene web that may have a basis weight of from about 0.2 to 0.8 oz./yd$^2$.; a liquid-impervious barrier 36, for example, a commercially available plastic film of polypropylene or the like; and an absorbent core 38 disposed therebetween. As shown in FIGS. 2 and 3, the absorbent structure 32 is in the form of a separate insert, typically of substantially non-stretchable materials, attached and integrated into the resiliently stretchable outer cover 12 using, e.g., autogenous bonds of the type generated thermally or ultrasonically, allowing substantially unrestricted functional stretchability of the outer cover. A preferably continuous ultrasonic or thermal perimeter bond 40 sealingly secures the absorbent structure 32 together to prevent leakage therefrom by bonding the liner 34 and barrier 36 peripherally to one another about the absorbent core 38 which is disposed therebetween. It is important that the materials of the barrier 36 and liner 34 be compatible with one another and with the material of the outer cover for autogenous bonding. Accordingly, polypropylene and other polyolefins have been found to be suitable materials for use in the liner, barrier and outer cover.

The outer cover 12 generally comprises an air-permeable, i.e., "breathable", elastomeric nonwoven laminar fabric wherein an elastic nonwoven web is joined to one or more gatherable nonwoven webs. Preferably, the laminate is resiliently stretchable from about 20 to about 200 percent in an essentially cross-body direction 41. The longitudinally opposed ears 20, 24; 22, 26 are fastenable and refastenable with one another substantially from the waist to the leg openings, preferably by utilizing a full-length, fixed-position fastening system of the type and in the manner disclosed in aforementioned copending U.S. Patent Application Ser. No. 902,828 filed Sept. 3, 1986, providing dimensional integrity to the resiliently stretchable garment during various and even extreme bodily movements and positions of the wearer. As shown in FIGS. 1-3, the preferred fastening system comprises a pair of fixed-position, full-length fastener members generally indicated at 43, 45, are situated on the internal bodyside surface of the rear pair of ear portions 20, 22 and a corresponding pair of the fastener members, generally indicated at 47, 49, are situated on the external surface of the rear pair of ear portions 24, 26. Referring to FIG. 1, the garment is secured about a wearer by positioning same under the wearer's body, then bringing the rear pair of ears 20, 22 around the waist of the wearer and positioning the rear pair of fasteners 43, 45 in fixed overlapping relationship with the longitudinally-opposed pair of front fasteners 47, 49, then fastening the cooperating elements together in the manner described in the aforesaid U.S. Application Ser. No. 902,828. Since the garment is form-fitting and self-adjusting, it does not gap or collapse at the hip and waist regions, as shown in FIGS. 4-7.

Preferably, the waist sections 13, 14 of the outer cover 12 have the insert 32 attached and integrated thereinto by attachment means according to the present invention as will be set forth more fully below.

As shown in FIGS. 2 and 2A, and with respect to the attachment means of the present invention, it is important to minimize the number of bonds and total bond area used in attaching and integrating the relatively unstretchable absorbent insert to the stretchable outer cover or, where forming waist hems as described herein, the number of bonds used to bond the outer cover to itself. The Applicants have discovered that the number of bonds correspondingly affects the stretch elongation in the elastomeric component that is bonded. Not only does a lesser number of bonds result in less stretch loss, but the greater the spacing apart of bond points, the less stretch elongation is affected. Accordingly, bonding patterns should be selected that significantly reduce the amount of stretch lost by means of the density and spacing of the bond points. Specifically, the lower the number and density of the integration bonds 51 for attaching and integrating the insert 32 along the waist sections 13, 14, the less stretch is inhibited along the waist opening thereby defined. For example, if the waist section is stretchable in a cross-body direction and the insert is attached thereto at two points lying on a line extending also in said cross-body direction, then the stretchability of the outer cover waist section along that line is restricted between those two points of attachment by the least stretchable element present between those points, usually either of the liner and barrier components of the insert. The insert may also be similarly attached and integrated adjacent the crotch section as described below.

Therefore, the garment of the present invention includes attachment means for attaching and integrating an absorbent insert structure, used for absorbing and containing body wastes, into a relatively stretchable elastomeric outer cover used for positioning the insert in bodily registration, while allowing substantially unrestricted functional stretchability thereof, maintaining the total garment anatomically form-fitting and generally self-adjusting.

The construction of the instant garment 10 is shown in greater detail in FIGS. 2-3. The opposed longitudinal ends 48, 50 of the absorbent insert 32 are attached and integrated to said outer cover 12 at selected front 52 and rear 54 waist attachment zones along said front 13 and rear 14 waist sections, respectively, defining one or more free-span zones 56 underlying said insert 32 wherein the functional stretchability of said outer cover in said free-span zone 56 is substantially unrestricted. It will be understood that where the insert 32 is integrated only at the waist attachment zones 52, 54 (not shown), the free-span zone underlies the entire span between the opposed longitudinal ends 48, 50 of the absorbent insert 32. Significantly, the free-span zone 56 also includes those portions of the waist sections 13, 14 not included in the waist attachment zones 52, 54. It will also be understood that the insert 32 may be adequately held by the outer cover 12 in registration with the body of the wearer without additional bonding in the free-span zone 56 to the front 28 or rear 30 panels or the crotch section 16. Moreover, substantially unrestricted functional stretchability of the outer cover, even in the waist attachment zones 52, 54, can be furthered by the instant invention as hereinafter set forth.

Referring again to FIGS. 2 and 3, additional elastication or bonding between other areas of the outer cover 12 and absorbent insert 32 may be provided for further contour and fit. Specifically, supplemental leg elastics 58 may be applied to outermost portions of the crotch section 16 around the inner curvature of the leg openings 18 to gather the garment 10 about the thighs of the wearer. Crotch elastics 60 may be applied to the liner 34 to cause the insert to more closely conform to the contours of the wearer's perineal region.

The leg elastics 58 preferably comprise a breathable elastomeric nonwoven laminate of the type described in copending U.S. patent application Ser. No. 947,949, assigned to the instant assignee, the entire disclosure of which is hereby incorporated by reference and relied upon. The leg elastic members 58 function cooperably with the stretchable outer cover for gathering the leg openings 18 about the wearer and can be applied in varying tensions relative thereto by adhesive, autogenous or pressure bonding. Leg hems (not shown) may alternatively be formed at the curved leg openings 18 in addition to the waist sections 13, 14, resulting in increased tension due to the increased thickness of the elastomeric material of the outer cover at the folded over hem. Alternatively, additional elastic members (not shown) of, e.g., FULLASTIC®, a trademarked extruded elastomeric film material sold by H. B. Fuller Company of Minneapolis, Minn., can be entrapped within the waist hems 66 and optional leg hems (not shown) to provide elastic gathering. Although the waist sections 13, 14 have heretofore discussed in conjunction with waist hems 66, a nonwoven elastomeric laminar material of the type described herein for the leg elastics 58 could be applied as a border strip (not shown) along the waist opening.

Although the free-span zones 56 can be provided in either of the front 28 and rear 30 panels, it is the stretch properties of the rear panel 30, which are more important. It should be noted, that cross-body stretch in the crotch section 16 of the outer cover 12 during use is minimally required so that bonding of the insert at or near the leg openings 18 of the crotch section 16 does not significantly affect the overall cross-body stretch properties of the outer cover. The breathable outer cover 12, among other functions, holds the insert 32 in proper bodily registration and, unlike the prior art, is not itself required to provide a liquid waste containment barrier.

Referring to FIG. 3, the absorbent insert 32 may further comprise at least one but preferably a pair of front 62 and rear 64 waist attachment flaps respectively situated at the opposed longitudinal ends 48, 50 of the insert 32. The flaps 62, 64 extend longitudinally from and contiguous with the liner 34 beyond the terminal ends of the absorbent composite 38, the flaps being bonded or otherwise attached to said front 13 and rear 14 waist sections, respectively, in said waist attachment zones 52, 54. The front 13 and rear 14 waist sections preferably have finished waist hems 66 along the waist opening wherein the waist attachment flaps 62, 64 are entrapped and bonded. The waist hems 66 comprise inwardly folded-over edges of outermost portions of said waist sections 13, 14.

Accordingly, the waist attachment flaps 62, 64 (FIGS. 2A and 3) may comprise coextensions of the barrier 36 and liner 34 or may comprise extensions of either the barrier 36 or liner 34 alone. The flaps 62, 64 typically comprise nonwoven and/or plastic film materials that are not inherently stretchable relative to the outer cover; however, the flaps 62, 64 themselves need not be contiguous with the liner or barrier material.

Even after attachment and integration of the insert 32 in the waist attachment zones, the outermost portions of the waist attachment flaps 48, 50 may still remain loose and unattached, possibly interfering during manufacturing and packaging processes or prior to wear when the garment is put on a wearer. Moreover, loose portions of the waist attachment flaps 48, 50 may lend an unaesthetic appearance to the garment before its application onto the wearer. Similarly, the lateral edges 53 of the absorbent insert 32 may tend to project outwardly into view from the leg openings during wear, especially by a smaller sized individual, detracting from the neat panty-like appearance of the garment. Even though trimming of the loose material from the waist attachment flaps 48, 50 and lateral edges 53 of the insert 32 may be ameliorative, a certain amount of material is still needed in the waist attachment flaps 48, 50 to, among other functions, aid in holding the insert in place, contribute to the aesthetic appearance of the garment during its application onto the wearer and provide stability to the product during processing and storage.

Figure 8:
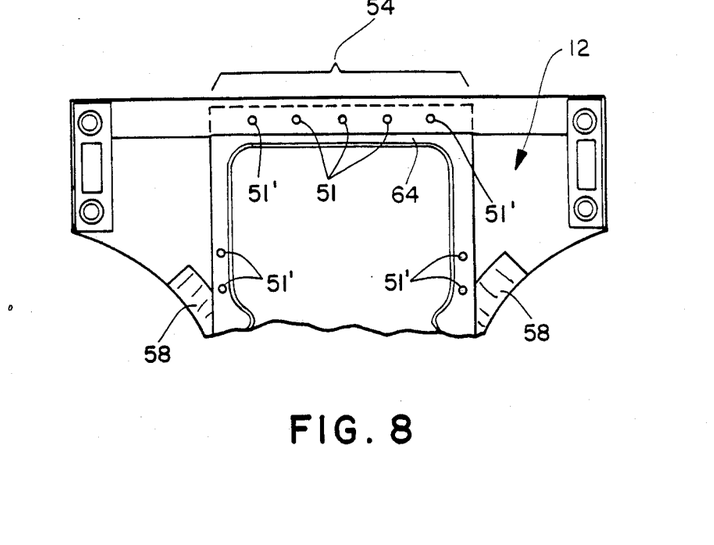
FIG. 8 is a partial plan view.
Figure 9:
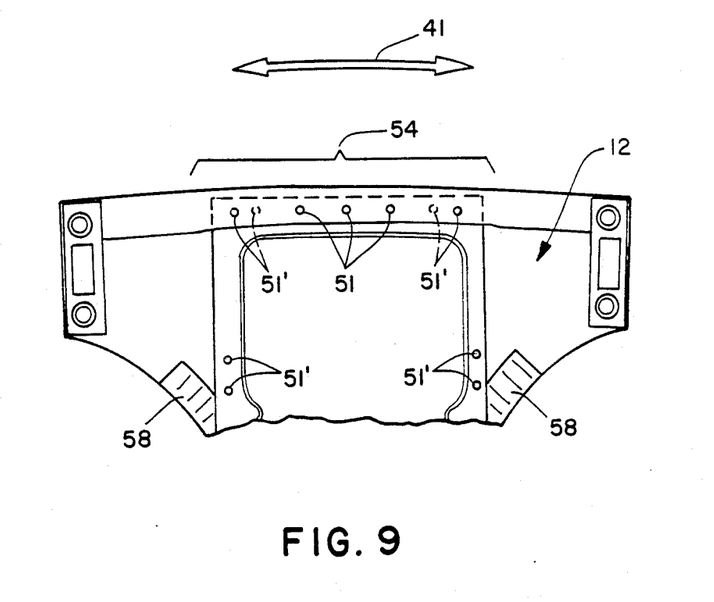
FIG. 9 is a sequential view of FIG. 8.

Referring to FIGS. 8 and 9 according to the instant invention, a combination of functionally permanent 51 and breakable 51' autogenous bonds are provided in order to minimize the restriction of stretch properties in the waist sections of outer cover 12 when the insert 32 is attached thereto. Permanently functional integration bonds 51 are placed only in the central portion of the waist attachment zones 52, 54 and stress release means, in the form of the breakable bonds 51', are used for integrating the insert 32 at outermost lateral portions of one or both of the waist attachment zones 52, 54 and are used along the lateral edges 53 of the insert 32 to conceal the lateral edges underneath the outer cover 12. The breakaway bonds 51' address the above-stated functional objectives as follows:

First, by holding the absorbent insert 32 in place during manufacture, storage, packaging and initial wear.

Second, when the garment 10 is in an unstretched condition prior to wear, the breakaway bonds 51' neatly conceal outermost lateral portions of the longitudinally opposed ends 52, 54 of the insert 32, e.g., by bonding the ends 52, 54 within the waist hems 66, for a more neat aesthetic appearance prior to wear, thereby minimizing any loose, unattached portions of the waist attachment flaps 48, 50.

Third, the breakaway bonds 51' allow further expansion of the elastomeric waist opening to more comfortably accommodate various body sizes and shapes. The breakaway bonds 51' may be effected at outermost lateral portions of both the front 52 and rear 54 waist attachment zones, as shown in FIG. 2 especially in the rear panel 30 operatively associated with the rear waist section 14, where stretch capability is generally more important.

Fourth, the breakable bonds 51' conceal the lateral edges 53 of the insert 32 underneath the outer cover and keep the edges 53 from extending outwardly from the leg openings 18, especially during wear by a smaller sized individual. Where greater stretch capacity is needed adjacent the leg openings, the breakable bonds 51' selectively break to allow accommodation of the larger sized body. The increased outer cover stretch once the breakable bonds 51' are broken at the lateral edges 53, itself effectively conceals those lateral edges underneath the outer cover 12. The lateral edges 53 of the insert 32 may have breakable bonds at the lower portions of either of the front 28 and rear 30 panels near the leg opening 18 at points that would be adjacent the frontal and outer hip curvatures of a wearer's legs, as shown in FIG. 2. For wearers having smaller sized legs, these breakable bonds between insert and outer cover adjacent the leg openings will remain intact, thereby limiting stretch properties which are not desirable for small leg sizes; however, during wear, larger leg sizes will selectively cause breakage of these bonds to provide greater stretch capability and more comfort to the wearer around the leg openings of the garment.

The breakaway bonds are preferably accomplished by providing an autogenous bond point having a smaller surface area or alternatively, by use of less bonding power from, e.g., thermal or ultrasonic bonding apparatus. When greater stretch capability is required during wear, the bonds 51' break with minimal detriment to the outer cover, thereby more fully allowing usage of outer cover stretch properties. Alternatively, the breakaway bonds 51' may also be accomplished by the use of an elastomeric nonwoven outer cover of the type disclosed herein, comprising a laminate wherein one or more layers thereof are not compatible for autogenous bonding purposes with the material of the component, e.g., the absorbent insert, being bonded to the outer cover. For this purpose, the outer cover of the invention may include an elastic nonwoven core layer which is autogenously bondable to the material of the absorbent insert, while the one or more gatherable nonwoven outer layers are not autogenously bondable to the insert. The breakaway bonds 51' are relatively stable until the outer cover is stretched and a sufficient shear force applied to the bonds 51', causing the bonds 51' to break and return the inherent functional stretch properties to the outer cover.

Another use of stress-release means of the type hereinabove described are for selectively allowing additional stretch capability along the leg elastics 58 themselves, accommodating different leg sizes and shapes. This result may be accomplished separately or in combination with the bonds 51', maintaining the lateral edges 53 of the insert concealed from view. Breakable bonds may be used intermediately along the leg elastics 58. The hereinabove described breathable elastomeric nonwoven laminar leg gathers may be applied in a tensioned state along the leg openings of the outer cover by means of autogenous bonds therebetween; specifically, the leg gathers may be bonded intermediately along their length by the breakable bonds 51''. The breakable bonds 51'', which are spaced closely together, remain intact when the garment is worn by individuals having smaller leg sizes, in which case, the closely spaced bonds 51'' minimize the elastic retractibility of the leg gathers 58 in the region surrounding the inner thigh. However, for larger sized legs requiring correspondingly greater stretch capacity as the garment is put on and worn, the breakable bonds 51'' are selectively broken away, with minimal accompanying degradation of the component materials, whereupon elastic retraction is increased and, as a result, greater stretch capacity is restored around the leg openings of the garment.

As can be seen in FIG. 3, the barrier 36 closely surrounds the bottom 68, and sides 70 of the absorbent core 38 (shown in phantom) with the liner 34 extending across and contacting the top surface of the absorbent core 38, imparting a generally rectangular boat-shaped configuration to the insert 32. The bottom 68 of the barrier 36 may include one or more relaxed localized areas adjacent the bottom 68 of the absorbent core 38 to accommodate swelling of the core during use with, for example, a hydrogel material. The perimeter bond 40 between the liner 34 and barrier 36 substantially around the absorbent core 38 may comprise either intermittent bonds or, preferably, a continuous autogenous bond. The perimeter bond 40 may be undulatory along the intermediate portion of the core 38, imparting a scalloped edge and greater flexibility therein.

Significantly, the absorbent structure 32 may be integrated into the outer cover 12 in the waist attachment zones 52, 54 while the outer cover is stretched in the cross-body direction 41. Preferably, the longitudinal length of the free-span zone 56 in the front 28 and rear 30 panels is at least about 2.5 inches or the longitudinal length of the fastener members 43, 45 and 47, 49, respectively.

A preferred method of integrating the absorbent insert structure 32 into the resiliently stretchable breathable outer cover 12 and assembling the instant disposable absorbent undergarment comprises the steps of providing the outer cover with opposed front 13 and rear 14 waist sections, a central crotch section 16, front 28 and rear 30 panels between the crotch and the waist sections prestretching the outer cover more than about 20% in a cross-body direction 41 parallel to the waist sections while superposing the insert 32 upon an inner surface of the outer cover, then bonding the longitudinally opposed ends 62, 64 of the insert to the waist sections in the selected waist attachment zones 52, 54, defining one or more free-span zones 56 allowing substantially unrestricted functional stretchability of the outer cover 12 underlying the free-span zones 56. One aspect of the present integration method comprises the step of inwardly folding over the outermost edges of the waist sections 13, 14 forming waist hems 66 entrapping the longitudinally opposed ends 62, 64 of the absorbent insert therein and bonding the opposed ends 62, 64 of the insert within the waist hems 66 at the waist attachment zones 52, 54.

FIGS. 4–7 show a disposable diaper 10 of the instant invention as it would be worn by a baby wherein the disposable diaper has a neat, trim fit and appearance when viewed from different perspectives.

Figure 7:
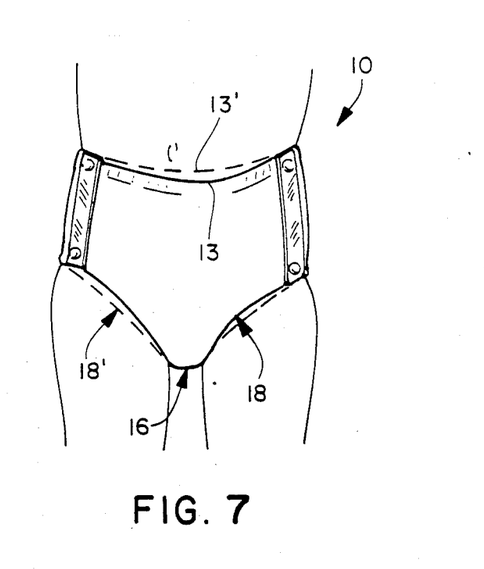
FIG. 7 is a front view of the disposable absorbent undergarment of the present invention showing the disposition of the garment on the baby after being worn for a period of time.

FIG. 7 illustrates the dimensional integrity of the diaper, as shown by the minimal extent the diaper moves or sags from an initial position as indicated by the dashed lines 18' and 13' after being worn by an infant for a period of time.

Turning now to the outer cover 12 of the present invention, which is preferably made from a resiliently stretchable elastomeric nonwoven laminar material having a stretchability of from about 20 percent to about 200 percent. The term stretchability as used herein is defined by the following relationship:

stretchability = ((final dimension − initial dimension)/initial dimension) × 100%

Since the outer cover 12 is also resilient, the outer cover returns essentially to its initial dimension when the stretching force is removed.

One such resiliently stretchable material is disclosed in U.S. patent application, Ser. No. 760,698 in the name of Tony J. Wisneski and Michael T. Morman, assigned to the assignee of the present application, entitled "Polyolefin-containing Extrudable Compositions and Methods for their Formation Into Elastomeric Products", the disclosure of which is incorporated herein by reference and relied upon. That application provides extrudable elastomeric compositions which, after extrusion, solidify to form elastomeric products such as, for example, fibrous nonwoven elastomeric webs. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A" and "A'" thermoplastic styrenic moiety containing endblocks of the block copolymer are selected from the group including polystyrene and polystyrene homologs such as, for example, poly(alpha-methylstyrene). In some embodiments the "A" and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight, of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures of from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature and elevated pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.1 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is extruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch, gage, to about 10 pounds per square inch, gage. The thread attenuating gas stream may be an inert, non-oxidizing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. Patent Application, Ser. No. 760,437 in the name of Jack D. Taylor and Michael J. Vander Wielen and assigned to the assignee of the present application, entitled "Composite Elastomeric Material and Process for Making the Same", the disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding, at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one gatherable web which is extensible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded locations. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymer endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alpha methylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basis weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. patent application, Ser. No. 760,449, in the name of Michael J. Morman, and assigned to the assignee of the present invention, entitled "Composite Nonwoven Elastic Web", the disclosure of which is incorporated herein by reference. That application is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, non-stretched length so as to gather the fibrous nonwoven gathered web. An important feature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spunbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, at this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The application also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure to the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with th contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. Patent Application Ser. No. 760,449 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyrene or polystyrene homolog endblock as "A'". The tacky fibrous nonwoven elastic web is then elongated by being stretched to an elongated, stretched length and a fibrous nonwoven gatherable web is formed, for example, by meltblowing or spunbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. Patent Application, Ser. No. 760,449 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, nonstretched state, is composed of a nonwoven elastic web that is joined to a fibrous nonwoven gathered web which has been gathered as a result of the nonwoven elastic web having been relaxed from an elongated stretched, biased length to a relaxed, unbiased nonstretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A" may be the same thermoplastic polymer endblock as "A'", such as a poly(vinyl arene), and where "B" is an elastomeric polymer midblock such as a conjugated diene or a lower alkene or (b) blends of one or more polyolefins or poly(alpha-methyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylene-butylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

As used in the U. S. Patent Application Ser. No. 760,449, and as contemplated herein, the term "nonwoven web" or "nonwoven layer" includes any web of material which has been formed without use of textile weaving processes which produce a structure of individual fibers which are interwoven in an identifiable repeating manner. Specific examples of nonwoven webs would include, without limitation, a meltblown nonwoven web, a spunbonded nonwoven web, an apertured film, a microporous web, elastomeric netting or a carded web of staple fibers.

It is to be clearly understood that the descriptions of methods for making a material suitable for outer cover 12 and the description of materials suitable for the outer cover 12 are exemplary only and not meant to be limiting.

The bodyside liner 34 may be airlaid, a bonded carded web, a powder-bonded carded web or a pattern bonded, spunbonded web of synthetic fibers such as polypropylene, polyester and the like.

Various materials are contemplated for use as the absorbent core 38, including fibrous materials, foams, particulates, etc. In general, the most economical liquid absorbent material for use in disposable diapers has been an absorbent fiber. The absorbent fiber most commonly used is cellulosic fiber such as comminuted wood pulp, commonly known in the art as "pulp fluff ," or simply "fluff."

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company. Other softwood fluffs may be purchased from Kimberly-Clark Corporation, such as CR-54. Various hardwood fluffs may also be blended with the softwood fluffs to form the absorbent composite. A water-swellable hydrogel material, preferably in particulate form, may be used in a number of various arrangements within the absorbent composite in order to decrease the bulkiness and enhance the capacity of the composite 38. It should be understood that additional elements could be provided in conjunction with those already set forth, without departing from the contemplated scope of the present invention and the description herein is not intended to be in any way limiting.

We claim:

1. An anatomically form-fitting, generally self-adjusting disposable absorbent garment comprising:

a breathable elastomeric nonwoven outer cover, including a pair of leg openings, front and rear waist sectioned together defining a waist opening, a crotch section situated between said leg openings and opposed front and rear panels separated by said crotch section;

an absorbent insert structure substantially superposable on said front and rear panels and said crotch section, including a liquid impermeable barrier, and a liquid permeable bodyside liner with an absorbent core disposed therebetween, delimiting opposed longitudinal ends and delimiting opposed lateral edges of said insert;

attachment means for attaching and integrating said longitudinal ends of said insert to said outer cover, at selected front and rear waist attachment zones, allowing substantially unrestricted functional stretchability of said outer cover and including stress-release means for selectively detaching said attachment means from said outer cover in either of said front and rear waist attachment zones and controlling the degree of elongation and contraction of the outer cover while maintaining the integration of said insert to the cover.

2. The invention of claim 1 further comprising one or more free-span zones underlying said insert wherein the functional stretchability of said outer cover is substantially unrestricted.

3. The invention of claim 2 wherein said stress-release means are situated at outermost lateral portions of at least said rear waist attachment zone.

4. The invention of claim 3 wherein said stress-release means attach said lateral edges of said insert to said outer cover in either of said front and rear panels and said crotch section, concealing said lateral edges from view underneath said outer cover while allowing selective detachment of said lateral edges from said outer cover when further enhancement of the stretchability of said outer cover is required.

5. The invention of claim 1 or 3 further comprising elastic nonwoven leg gathers applied in a tensional condition to said outer cover along said leg openings and wherein said stress-release means attach said leg gathers intermediately along the length thereof to said outer cover, limiting the retractability of said leg gathers and said outer cover along said intermediate attachments while allowing selective detachment between said leg gathers and said outer cover when further enhancement of stretchability along said leg openings is required.

6. The invention of claim 1, 2, 3 or 4 wherein said attachment means comprise autogenous bonds of the type generated thermally or ultrasonically.

7. The invention of claim 6 wherein said stress-release means comprise functionally breakable autogenous bonds.

8. The invention of claim 7 wherein the autogenous bonds comprising said stress-release means are of a lesser strength than the autogenous bonds comprising the attachment means, allowing selective separation of said insert from said outer cover only at said stress-release bond sites.

9. The invention of claim 1 wherein said outer cover comprises an elastic nonwoven web joined to one or more gatherable nonwoven webs.

10. The invention of claim 5 wherein said leg gathers comprise an elastic nonwoven web joined to one or more gatherable nonwoven webs.

* * * * *